US007289761B2

(12) United States Patent
Mazar

(10) Patent No.: US 7,289,761 B2
(45) Date of Patent: Oct. 30, 2007

(54) SYSTEMS, DEVICES, AND METHODS FOR SELECTIVELY PREVENTING DATA TRANSFER FROM A MEDICAL DEVICE

(75) Inventor: Scott T. Mazar, Inver Grove Heights, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 490 days.

(21) Appl. No.: 10/601,966

(22) Filed: Jun. 23, 2003

(65) Prior Publication Data

US 2004/0259494 A1 Dec. 23, 2004

(51) Int. Cl.
*H04K 3/00* (2006.01)
*A61N 1/08* (2006.01)
*A61B 5/0428* (2006.01)

(52) U.S. Cl. ............................ 455/1; 607/60; 600/508

(58) Field of Classification Search .................... 455/1, 455/404.1, 404.2, 456.1; 607/32, 31, 60; 600/300, 508

See application file for complete search history.

(56) References Cited

U.S. PATENT DOCUMENTS

| | | | | |
|---|---|---|---|---|
| 5,390,238 | A | 2/1995 | Kirk et al. | 379/93 |
| 5,416,695 | A | 5/1995 | Stutman et al. | 364/413.02 |
| 5,576,952 | A | 11/1996 | Stutman et al. | 364/413.02 |
| 5,713,937 | A | 2/1998 | Nappholz et al. | 607/30 |
| 5,716,382 | A | 2/1998 | Snell | 607/30 |
| 5,722,999 | A | 3/1998 | Snell | 607/32 |
| 5,724,580 | A | 3/1998 | Levin et al. | 395/615 |
| 5,807,336 | A * | 9/1998 | Russo et al. | 604/131 |
| 6,055,506 | A | 4/2000 | Frasca, Jr. | 705/3 |
| 6,085,096 | A * | 7/2000 | Nakamura | 455/456.6 |
| 6,131,045 | A * | 10/2000 | Iwata | 340/7.39 |
| 6,171,237 | B1 | 1/2001 | Avitall et al. | 600/300 |
| 6,171,264 | B1 | 1/2001 | Bader | 600/595 |
| 6,201,973 | B1 * | 3/2001 | Kowaguchi | 455/456.6 |
| 6,203,495 | B1 | 3/2001 | Bardy | 600/301 |
| 6,221,011 | B1 | 4/2001 | Bardy | 600/300 |
| 6,249,705 | B1 | 6/2001 | Snell | 607/59 |
| 6,261,230 | B1 | 7/2001 | Bardy | 600/300 |
| 6,302,844 | B1 | 10/2001 | Walker et al. | 600/300 |
| 6,312,378 | B1 | 11/2001 | Bardy | 600/300 |
| 6,331,160 | B1 | 12/2001 | Bardy | 600/300 |
| 6,336,903 | B1 | 1/2002 | Bardy | 600/508 |
| 6,368,284 | B1 | 4/2002 | Bardy | 600/508 |

(Continued)

*Primary Examiner*—Tilahun Gesesse
(74) *Attorney, Agent, or Firm*—Schwegman, Lundberg, & Woessner, P.A.

(57) ABSTRACT

Systems and methods provide for the selective prevention of data transfer from a medical device to allow the patient to have privacy when desired. Theses systems and methods provide medical devices that can be instructed in various ways to stop recording data and/or transmitting data to external devices and systems. These systems and methods also provide external repeater devices that can also be instructed in various ways to stop recording data being received, stop forwarding data that is being or has already been received, and/or to stop soliciting data from the medical device. These systems and methods also provide for a blocking device that may be separate from the medical device and repeater to provide instruction to the medical device and/or repeater to prevent data transfer such as by stopping the recording or transmission of data. Further, the blocking device may be alternatively configured to provide a jamming signal to prevent data transmissions from being successfully communicated between the medical device and the repeater.

26 Claims, 7 Drawing Sheets

U.S. PATENT DOCUMENTS

| | | | | |
|---|---|---|---|---|
| 6,398,728 | B1 | 6/2002 | Bardy | 600/300 |
| 6,411,840 | B1 | 6/2002 | Bardy | 600/513 |
| 6,471,645 | B1 * | 10/2002 | Warkentin et al. | 600/300 |
| 6,985,773 | B2 * | 1/2006 | Von Arx et al. | 607/32 |
| 7,039,426 | B2 * | 5/2006 | Naiki | 455/456.4 |
| 2001/0011153 | A1 | 8/2001 | Bardy | 600/300 |
| 2001/0021801 | A1 | 9/2001 | Bardy | 600/300 |
| 2001/0025137 | A1 | 9/2001 | Webb et al. | 600/300 |
| 2001/0025138 | A1 | 9/2001 | Bardy | 600/300 |
| 2001/0037056 | A1 | 11/2001 | Nunome | 600/300 |
| 2001/0039375 | A1 | 11/2001 | Lee et al. | 600/301 |
| 2001/0044588 | A1 | 11/2001 | Mault | 600/549 |
| 2001/0051764 | A1 | 12/2001 | Bardy | 600/300 |
| 2001/0051765 | A1 | 12/2001 | Walker et al. | 600/300 |
| 2002/0013538 | A1 | 1/2002 | Teller | 600/549 |
| 2002/0019584 | A1 | 2/2002 | Schulze et al. | 600/300 |
| 2002/0022776 | A1 | 2/2002 | Bardy | 600/300 |
| 2002/0026103 | A1 | 2/2002 | Norris et al. | 600/300 |
| 2002/0026104 | A1 | 2/2002 | Bardy | 600/300 |
| 2002/0028988 | A1 | 3/2002 | Suzuki et al. | 600/300 |
| 2003/0143943 | A1 * | 7/2003 | Kline | 455/1 |

* cited by examiner

SYSTEMS, DEVICES, AND METHODS FOR SELECTIVELY PREVENTING DATA TRANSFER FROM A MEDICAL DEVICE

TECHNICAL FIELD

The present system relates generally to advanced patient management systems, and particularly, but not by way of limitation, to such a system whereby data transfer from a medical device to an external device is selectively prevented.

BACKGROUND OF THE INVENTION

Management of patients with chronic disease consumes a significant proportion of the total health care expenditure in the United States. Many of these diseases are widely prevalent and have significant annual incidences as well. Heart failure prevalence alone is estimated at over 5.5 million patients in 2000 with incidence rates of over half a million additional patients annually, resulting in a total health care burden in excess of $20 billion. Heart failure, like many other chronic diseases such as asthma, COPD, chronic pain, and epilepsy, is event driven, where acute de-compensations result in hospitalization. In addition to causing considerable physical and emotional trauma to the patient and family, event driven hospitalizations consume a majority of the total health care expenditure allocated to the treatment of heart failure.

Hospitalization and treatment for an acute de-compensation typically occurs after the de-compensation event has happened. However, most heart failure patients, for example, exhibit prior non-traumatic symptoms, such as steady weight gain, in the weeks or days prior to the de-compensation. If the caregiver is aware of these symptoms, it is possible to intervene before the event, at substantially less cost to the patient and the health care system. Intervention is usually in the form of a re-titration of the patient's drug cocktail, reinforcement of the patient's compliance with the prescribed drug regimen, or acute changes to the patient's diet and exercise. Such intervention is usually effective in preventing the de-compensation episode and thus avoiding hospitalization.

Patients with health conditions can receive medical devices such as subcutaneously implanted medical devices, supercutaneously coupled medical devices, and/or medical devices otherwise coupled to the body. For example, chronic heart disease patients may receive medical devices such as pacemakers, implantable cardioverter defibrillators (ICDs), and heart failure cardiac resynchronization therapy (CRT) devices. Currently, the physician that installs pacemakers, ICDs, and/or other medical devices requires their patients to make clinic visits periodically, usually once every three or four months, in order to verify if their medical device is working correctly and programmed optimally. Device follow-ups are usually performed by the nurse-staff assisted by the sales representative from the device manufacturers. Device follow-ups are labor intensive and typically require patients to make multiple clinic visits.

In an effort to limit the number of follow-ups necessary to monitor the device and the data that it acquires, an advanced patient management system may provide a communication infrastructure. This infrastructure allows the medical device to communicate over long distances at virtually any time with a backend system that monitors the medical device and the patient. Furthermore, this backend system allows monitoring of the patient on a more frequent basis than ordinary follow-up visits can practically allow. The back end system may communicate with the medical device through an external unit such as a repeater that the patient keeps in close proximity. Conventionally for many medical devices, the external unit communicates directly with the medical device through an inductive coupling which requires that the patient hold a wand over the location of the medical device. Alternatively, short range radio frequency transfer may occur between the external device and the medical device. The external unit then transfers information from the medical device through a telephone line or other network interface to the back end system. Furthermore, it is likely that medical devices will employ longer range wireless telecommunication abilities to establish communication directly with the backend system through, for example, cellular networks.

The conventional approach to communicating with the medical device has drawbacks in that the patient lacks privacy due to the medical device recording data about the patient continuously or at pre-determined times. This data being recorded may include health related data but may also include other information, such as the location of the patient where the medical device incorporates a geonavigational positioning system or cellular phone technology. Additionally, this data may be streamed from the medical device to an external device where it is recorded and/or forwarded to the backend patient management system. The patient has little ability to control when the medical device is recording data that is subject to be transferred or when it is transmitting the data being recorded to the external devices and systems. Many patients likely prefer the ability to control such data transfer so that data about the patient is not always available for others to see, but such control is not possible with conventional systems.

SUMMARY OF THE INVENTION

Embodiments of the present invention address these problems and others by providing the patient with the ability to control the data transfer from the medical device to external devices and/or systems. The patient may control data transfer by controlling whether the medical device is recording data at a particular time so that data for this period is not available for immediate or delayed transfer. In alternative embodiments, the patient may control data transfer by controlling whether transmissions of data that it has already recorded or is in the process of recording may occur, such as by jamming signals that instruct the medical device to begin transmission or by providing signals to instruct that no transmission should occur.

One embodiment is a method for jamming communications between a medical device and an external device to prevent data transfer. The method involves receiving an external input at a blocking device to begin jamming the communications between the medical device and the external device. A jamming signal is transmitted from the blocking device to jam the communications between the medical device and the external device.

Another embodiment is a method for inhibiting communications between a medical device and an external device to prevent data transfer. The method involves receiving an external input to begin inhibiting the communications between the medical device and the external device. Upon receiving the input, the establishment of data transmission is ceased between the medical device and the external device.

Another embodiment is a method for inhibiting recording of physiological data sensed by an medical device to prevent data transfer. The method involves receiving an input to begin inhibiting the recording. Upon receiving the input, the recording of the data that is sensed by the medical device is ceased.

Another embodiment is a method for inhibiting communications involving data generated at an medical device between a local external device and a remote external device to prevent data transfer. The method involves receiving a data transmission from the medical device at the local external device and receiving an external input to begin inhibiting the communications between the local external device and the remote external device. Upon receiving the input, the establishment of data transmission from the local external device to the remote external device is ceased.

Another embodiment is a medical device which includes a communications system that sends and receives signals. At least one sensor is included that detects physiological information about a patient to produce data. A controller is configured to detect an input indicating that data transmission should cease, and to cease transmitting data through the communication system upon detecting the input.

Another embodiment is a medical device which includes a memory for recording data. At least one sensor is included that detects physiological information about a patient to produce data. A controller is configured to detect an input indicating that data recording should cease, and to cease recording data to the memory upon detecting the input.

Another embodiment is an external repeater device for communicating with a medical device which includes a communications system that sends and receives signals such that patient data is received from the medical device upon a solicitation for data being sent from the communications system. A controller is configured to detect an input indicating that data transmission should cease, and to cease transmitting the solicitation for data through the communications system to the medical device upon detecting the input.

Another embodiment is an external repeater device for communicating with a medical device which includes a communications system that sends and receives signals such that patient data is received from the medical device. A memory stores patient data received from the medical device, and a controller is configured to detect an input indicating that data recording should cease, and to cease recording to the memory the data received from the medical device upon detecting the input.

Another embodiment is a blocking device for preventing a medical device from receiving solicitations for data. The blocking device includes a transmitter that generates a jamming signal that is received by the medical device, wherein the jamming signal is generated during a period of time that a solicitation signal is present and wherein the reception of the jamming signal prevents reception of the solicitation signal by the medical device.

These and various other features as well as advantages, which characterize the present invention, will be apparent from a reading of the following detailed description and a review of the associated drawings.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

Prior to discussing the medical devices, external repeater devices, and blocking devices according to the embodiments of the present invention, an example of an advanced patient management system is discussed to provide an example of an environmental context for these embodiments. However, it is to be understood that the advanced patient management system described herein in conjunction with the embodiments of the present invention is only one example of an operating environment and is not to be taken in a limiting sense. For example, the embodiments of the present invention involving communication between an external repeater device and a medical device may operate without further interaction with an advanced patient management system and its associated communication system. The devices and communication protocols of the embodiments of the present invention are discussed below with reference to FIGS. 5-10 in section V. Preventing Data Transfer.

An advanced patient management system is configured to collect patient-specific information, store and collate the information, and generate actionable recommendations to enable the predictive management of patients. The advanced patient management system is also configured to leverage a remote communications infrastructure to provide automatic device follow-ups to collect data, coordinate therapy, and to determine if remote devices are functioning properly. The term “patient” is used herein to mean any individual from whom information is collected. The term “caregiver” is used herein to mean any provider of services, such as health care providers including, but not limited to, nurses, doctors, and other health care provider staff.

Figure 1:
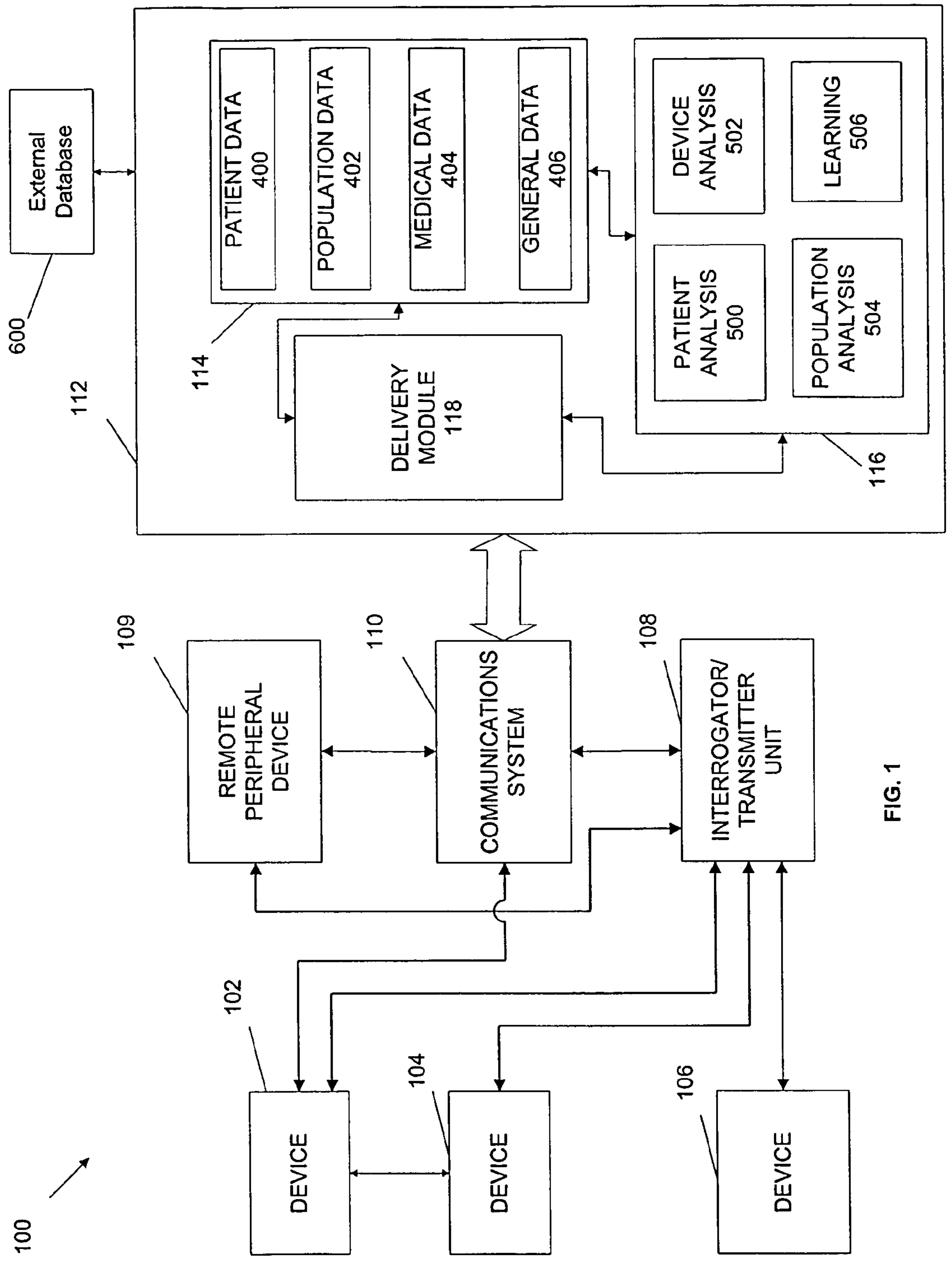
FIG. 1 illustrates an advanced patient management system.

FIG. 1 illustrates an example advanced patient management system 100. Advanced patient management system 100 generally includes the following components: one or more devices 102, 104, and 106, one or more interrogator/ transceiver units 108, a communication system 110, one or more remote peripheral devices 109, and a host 112.

Each component of the advanced patient management system 100 can communicate using the communication system 110. Some components may also communicate directly with one another. For example, devices 102 and 104 may be configured to communicate directly with one another. The various components of the example advanced patient management system 100 illustrated herein are described below.

I. Devices

Devices 102, 104, and 106 can be subcutaneously implanted medical devices, supercutaneously implanted medical devices, medical devices otherwise coupled to a patient, or external devices that may provide one or more of the following functions with respect to a patient: (1) sensing, (2) data analysis, and (3) therapy. For example, in one embodiment, devices 102, 104, and 106 are either subcutaneoulsy, supercutaneously implanted, or otherwise externally coupled devices used to measure a variety of physiological, subjective, and environmental conditions of a patient using electrical, mechanical, and/or chemical means. The devices 102, 104, and 106 can be configured to automatically gather data or can require manual intervention by the patient. The devices 102, 104, and 106 can be configured to store data related to the physiological and/or subjective measurements and/or transmit the data to the communication system 110 using a variety of methods, described in detail below. Although three devices 102, 104, and 106 are illustrated in the example embodiment shown, more or fewer devices may be used for a given patient.

The devices 102, 104, and 106 can be configured to analyze the measured data and act upon the analyzed data. For example, the devices 102, 104, and 106 are configured to modify therapy or provide alarm indications based on the analysis of the data.

In one embodiment, devices 102, 104, and 106 also provide therapy. Therapy can be provided automatically or in response to an external communication. Devices 102, 104, and 106 are programmable in that the characteristics of their sensing, therapy (e.g., duration and interval), or communication can be altered by communication between the devices 102, 104, and 106 and other components of the advanced patient management system 100. Devices 102, 104, and 106 can also perform self-checks or be interrogated by the communication system 110 to verify that the devices are functioning properly. Examples of different embodiments of the devices 102, 104, and 106 are provided below.

Medical devices coupled to the body have the ability to sense and communicate as well as to provide therapy. Medical devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance.

A heart rhythm sensor, typically found in a pacemaker or defibrillator, is one example of a subcutaneously implantable medical device. In the heart, an electrical wave activates the heart muscle just prior to contraction. As is known in the art, electrical circuits and lead-wires transduce the heart's activation event and reject other, non-essential electrical events. By measuring the time interval between activation events, the heart rhythm can be determined. A transthoracic impedance sensor is another example of a sensor in an implantable medical device. During the respiratory cycle, large volumes of air pass into and out of the body. The electrical resistance of the thorax changes markedly as a result of large differences in conductivity of air and body tissues. The thoracic resistance can be measured during respiration and converted into a measurable electrical signal (i.e., impedance) so that breathing rate and profile can be approximated. Medical devices can also sense chemical conditions, such as glucose levels, blood oxygen levels, etc. Further, the advanced patient management system 100 may utilize other medical devices as well that provide physiological measurements of the patient, such as drug pumps, neurological devices (e.g., stimulators), oxygen sensors, etc.

Derived measurements can also be determined from the medical device sensors. For example, a sleep sensor can rely on measurements taken by an implanted accelerometer that measures body activity levels. The sleep sensor can estimate sleeping patterns based on the measured activity levels. Other derived measurements include, but are not limited to, a functional capacity indicator, autonomic tone indicator, sleep quality indicator, cough indicator, anxiety indicator, and cardiovascular wellness indicator for calculating a quality of life indicator quantifying a patient's overall health and well-being.

Medical devices 102, 104, and 106 can also be external devices, or devices that are not implanted in the human body, that are used to measure physiological data. Such devices include a multitude of devices to measure data relating to the human body, such as temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System (GPS)).

Devices 102, 104, and 106 can also be environmental sensors. The devices can be placed in a variety of geographic locations (in close proximity to patient or distributed throughout a population) and record non-patient specific characteristics such as, but not limited to, temperature, air quality, humidity, carbon monoxide level, oxygen level, barometric pressure, light intensity, and sound.

One or more of the devices 102, 104, and 106 (for example, device 106) may be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" The device can prompt the patient and record subjective data from the patient using visual and/or audible cues. For example, the patient can press coded response buttons or type an appropriate response on a keypad. Alternatively, subjective data may be collected by allowing the patient to speak into a microphone and using speech recognition software to process the subjective data.

In one example embodiment, the subjective device presents the patient with a relatively small number of responses to each question posed to the patient. For example, the responses available to the patient may include three faces representing feelings of happiness, nominalness, and sadness. Averaged over time, a trend of a patient's well being will emerge with a finer resolution than the quanta of the three responses.

The subjective data can be collected from the patient at set times, or, alternatively, collected whenever the patient feels like providing subjective data. The subjective data can also be collected substantially contemporaneously with physiological data to provide greater insight into overall patient wellness. The subjective device 106 can be any device that accepts input from a patient or other concerned individual and/or provides information in a format that is recognizable to the patient. Device 106 typically includes a keypad, mouse, display, handheld device, interactive TV, cellular telephone or other radio frequency ("RF") communications device, cordless phone, corded phone, speaker, microphone, email message, or physical stimulus.

Figure 2:
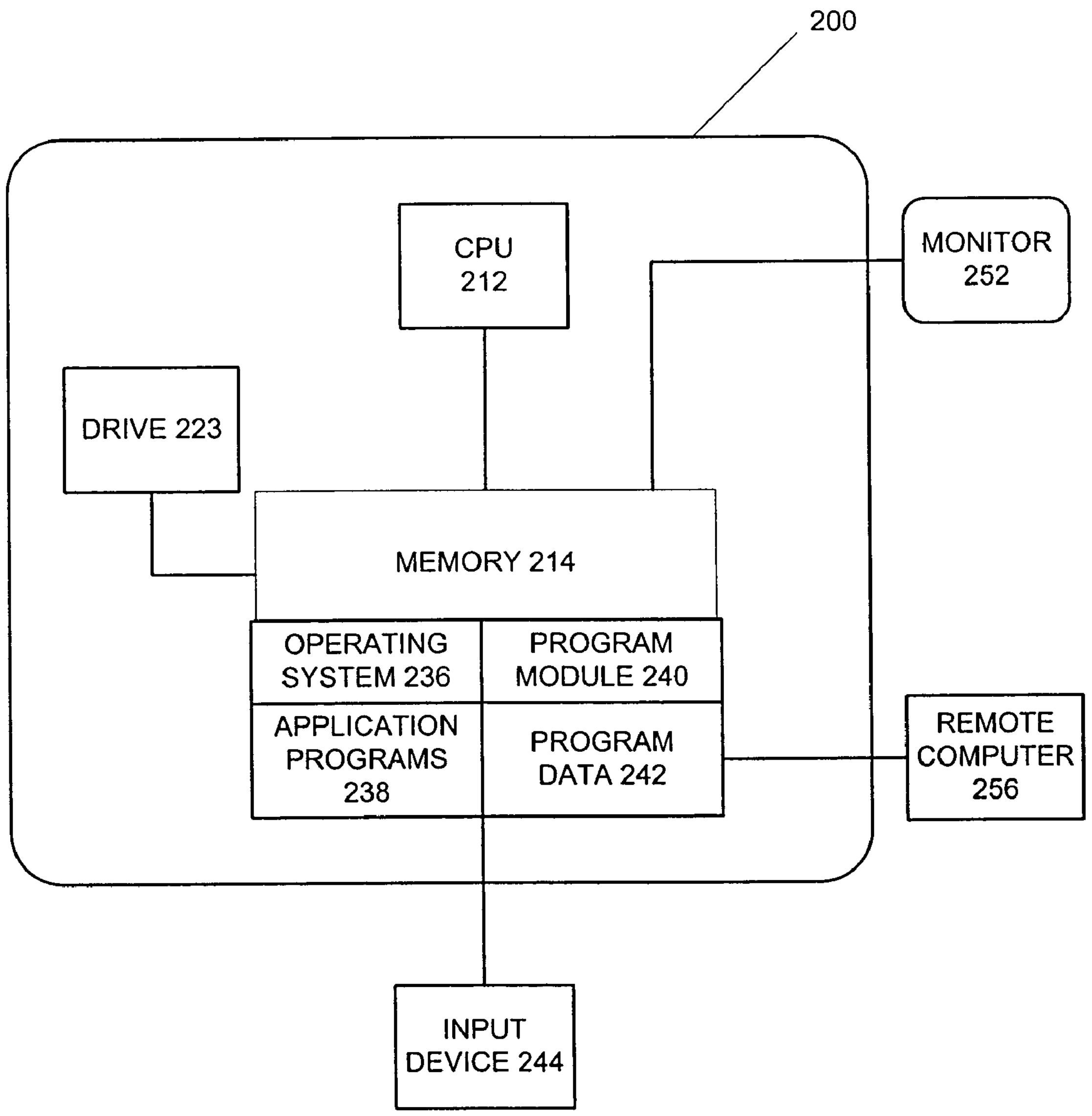
FIG. 2 illustrates an example computer system for use with the advanced patient management system.

In one example embodiment, the subjective device 106 includes or is part of a computer system 200, as illustrated in FIG. 2. The example computer system 200 includes a central processor unit 212 and a system memory 214. The computer system 200 further includes one or more drives 223 for reading data from and writing data to, as well as an input device 244, such as a keyboard or mouse, and a monitor 252 or other type of display device. A number of program modules may be stored on the drive 223, including an operating system 236, one or more application programs 238, other program modules 240, and program data 242. The computer system 200 can operate in a networked environment using logical connections to one or more remote computers or computer systems 256. Computer system 200 can also include hand-held computers such as a PDA computer.

The advanced patient management system 100 may also include one or more remote peripheral devices 109. The remote peripheral device 109 may include, for example and without limitation, cellular telephones, pagers, PDA devices, facsimiles, remote computers, printers, video and/or audio devices, etc. The remote peripheral device 109 can communicate using wired or wireless technologies and may be used by the patient or caregiver to communicate with the communication system 110 and/or the host 112. For example, the remote peripheral device 109 can be used by the caregiver to receive alerts from the host 112 based on data collected from the patient and to send instructions from the caregiver to either the patient or other clinical staff. In another example, the remote peripheral device 109 is used by the patient to receive periodic or real time updates and alerts regarding the patient's health and well-being.

II. Interrogator/Transceiver Unit

Figure 3:
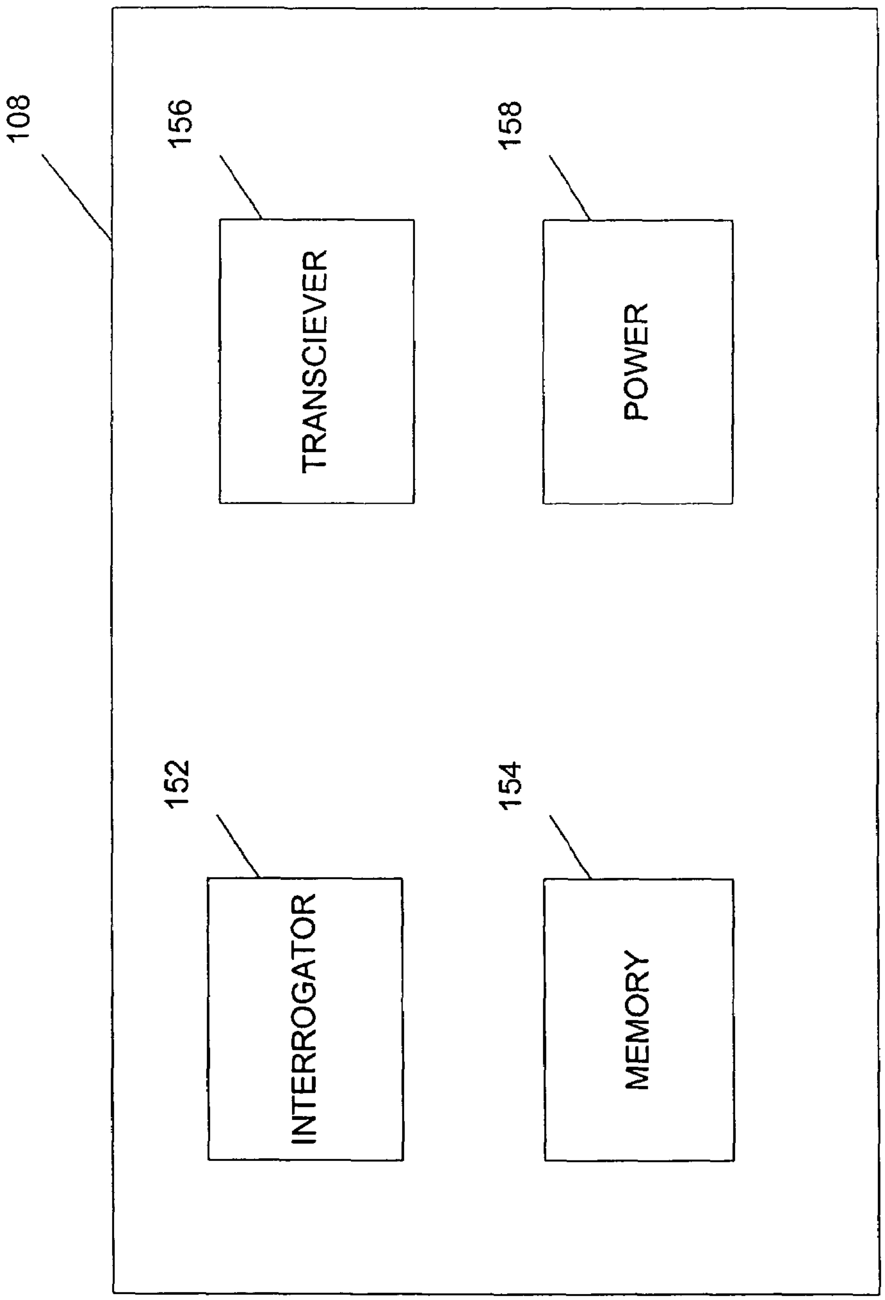
FIG. 3 illustrates an example interrogator/transceiver unit for use with the advanced patient management system.

Referring now to FIG. 3, the example advanced patient management system 100 includes one or more interrogator/transceiver units ("ITUs"), such as ITU 108. The ITU 108 includes an interrogator module 152 for sending and receiving data from a device, such as devices 102, 104, and 106, a memory module 154 for storing data, and a transceiver module 156 for sending and receiving data to and from other components of the APM system 100. The transceiver module may also operate as an interrogator of the devices 102, 104 and 106. The ITU 108 also includes a power module 158 that provides power.

The ITU 108 may perform one or more of the following functions: (1) data storage; (2) data analysis; (3) data forwarding; (4) patient interaction; (5) patient feedback; and (6) data communications. For example, the ITU 108 may facilitate communications between the devices 102, 104, and 106 and the communication system 110. The ITU 108 can, periodically or in real-time, interrogate and download into memory clinically relevant patient data from the devices 102, 104, and/or 106. This data includes, in the cardiac sensor context, for example, P and R-wave measurements, pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The data is sent to the ITU 108 by the devices 102, 104, and 106 in real-time or periodically uploaded from buffers in the devices.

The ITU 108 may also allow patient interaction. For example, the ITU 108 may include a patient interface and allow the patient to input subjective data. In addition, the ITU 108 may provide feedback to the patient based on the data that has been analyzed or based on information communicated by the communication system 110.

In another embodiment, the ITU 108 includes a telemetry link from the devices to a network that forms the basis of a wireless LAN in the patient's home. The ITU 108 systematically uploads information from the devices 102, 104, and/or 106 while the patient is sleeping, for example. The uploaded data is transmitted through the communication system 110 or directly to the host 112. In addition, in one embodiment the ITU 108 functions in a hybrid form, utilizing wireless communication when available and defaulting to a local wireless portal or a wired connection when the wireless communication becomes unavailable.

Some medical devices, such as legacy implanted cardiac rhythm management ("CRM") devices, communicate via an internal telemetry transceiver that communicates with an external programmer device. The communication range of such devices is typically 1 to 4 inches. ITU 108 may include a special short-range interrogator that communicates with a legacy medical device.

When the interrogator 152 uses radio frequency to communicate with the devices 102, 104, 106, the ITU 108 may be in the form of a small device that is placed in an inconspicuous place within the patient's residence. Alternatively, the ITU 108 may be implemented as part of a commonly-used appliance in the patient's residence. For example, the ITU may be integrated with an alarm clock that is positioned near the patient's bed. In another embodiment, the ITU may be implemented as part of the patient's personal computer system. Other embodiments are also possible.

In another embodiment, the ITU 108 may comprise a hand-held device such as a PDA, cellular telephone, or other similar device that is in wireless communication with the devices 102, 104, and 106. The hand-held device may upload the data to the communication system 110 wirelessly. Alternatively, the hand-held device may periodically be placed in a cradle or other similar device that is configured to transmit the data to the communication system 110.

In one embodiment, the ITU 108 can perform analysis on the data and provide immediate feedback, as well as perform a variety of self-diagnostic tests to verify that it is functioning properly and that communication with the communication system 110 has not be compromised. For example, the ITU 108 can perform a diagnostic loop-back test at a time set by the host 112, which involves sending a request through the communication system 110 to the host 112. The host 112 can then reply with a response back through the communication system 110 to the ITU 108. If a specific duration elapses before the ITU 108 receives the response or the ITU 108 receives an unexpected response, or if the host 112 does not receive the diagnostic test communication, the ITU 108 can provide indications that the system is not functioning properly and the host 112 can alert an operator that there may be compromised communications with that specific ITU 108. For example, if wireless communications between the ITU 108 and the communication system 110 have been interrupted, and the ITU 108 performs a self-diagnostic test that fails, the ITU 108 may alert the patient so that corrective action may be taken. The alert can take the form of a sound or a visual and/or audible annunciator to alert the patient that communication has been interrupted. In another embodiment, the ITU 108 can automatically fail-back to a wired system to communicate with the communication system 110 and perform the same communications compromise checks.

In other embodiments of the advanced patient management system 100, the ITU 108 function can be integrated into devices 102, 104, and 106, so that the devices can communicate directly with the communication system 110 and/or host 112. The devices 102, 104 and 106 can incorporate multi-mode wireless telecommunications such as cellular, BLUETOOTH, or IEEE 802.11B to communicate with the communication system 110 directly or through a local wireless to a wired portal in the patients' home. For example, device 102 may include a miniature cellular phone capable of wirelessly uploading clinical data from the device on a periodic basis. This is particularly advantageous for devices that are mobile (e.g., an implanted medical device in a patient that is traveling).

To conserve the energy of the devices 102, 104, and 106, particularly when the devices (e.g., device 102) are configured to communicate directly with the communication system 110 without using an ITU 108, in one example embodiment the devices are configured to communicate during a given duty cycle. For example, the device 102 can be configured to communicate with the communication system 110 at given intervals, such as once a week. The device 102 can record data for the time period (e.g., a week) and transmit the data to the communication system 110 during the portion of the cycle that transmission is active and then conserve energy for the rest of the cycle. In another example, the device 102 conserves energy and only communicates with the communication system 110 when an "interesting" event, such as a heart arrhythmia, has occurred. In this manner, device 102 can communicate directly with the communication system 110 and/or host 112 without requiring an ITU 108, while conserving the energy of the device by communicating only during a given duty cycle.

The interrogation rate of the ITU 108 can be varied depending on disease state and other relevant factors. In addition, the devices 102, 104, and 106 can be configured to "wake up" frequently (e.g., once every couple minutes) to provide the ITU 108 an access window for the ITU 108 to provide commands to the devices 102, 104, and 106, as well as upload data from the devices.

If multiple devices, such as devices 102, 104, and 106, are provided for a given patient, each device may include its own means for communicating with the ITU 108 or communication system 110. Alternatively, a single telemetry system may be implemented as part of one of the devices, or separate from the devices, and each device 102, 104, and 106 can use this single telemetry system to communication with the ITU 108 or the communication system 110.

In yet another embodiment, the devices 102, 104, and 106 include wires or leads extending from devices 102, 104, and 106 to an area external of the patient to provide a direct physical connection. The external leads can be connected, for example, to the ITU 108 or a similar device to provide communications between the devices 102, 104, and 106 and the other components of the advanced patient management system 100.

The advanced patient management system 100 can also involve a hybrid use of the ITU 108. For example, the devices 102, 104, and 106 can intelligently communicate via short-range telemetry with the ITU when the patient is located within the patient's home and communicate directly with the communication system 110 or host 112 when the patient is traveling. This may be advantageous, for example, to conserve battery power when the devices are located near an ITU.

III. Communication System

Figure 4:
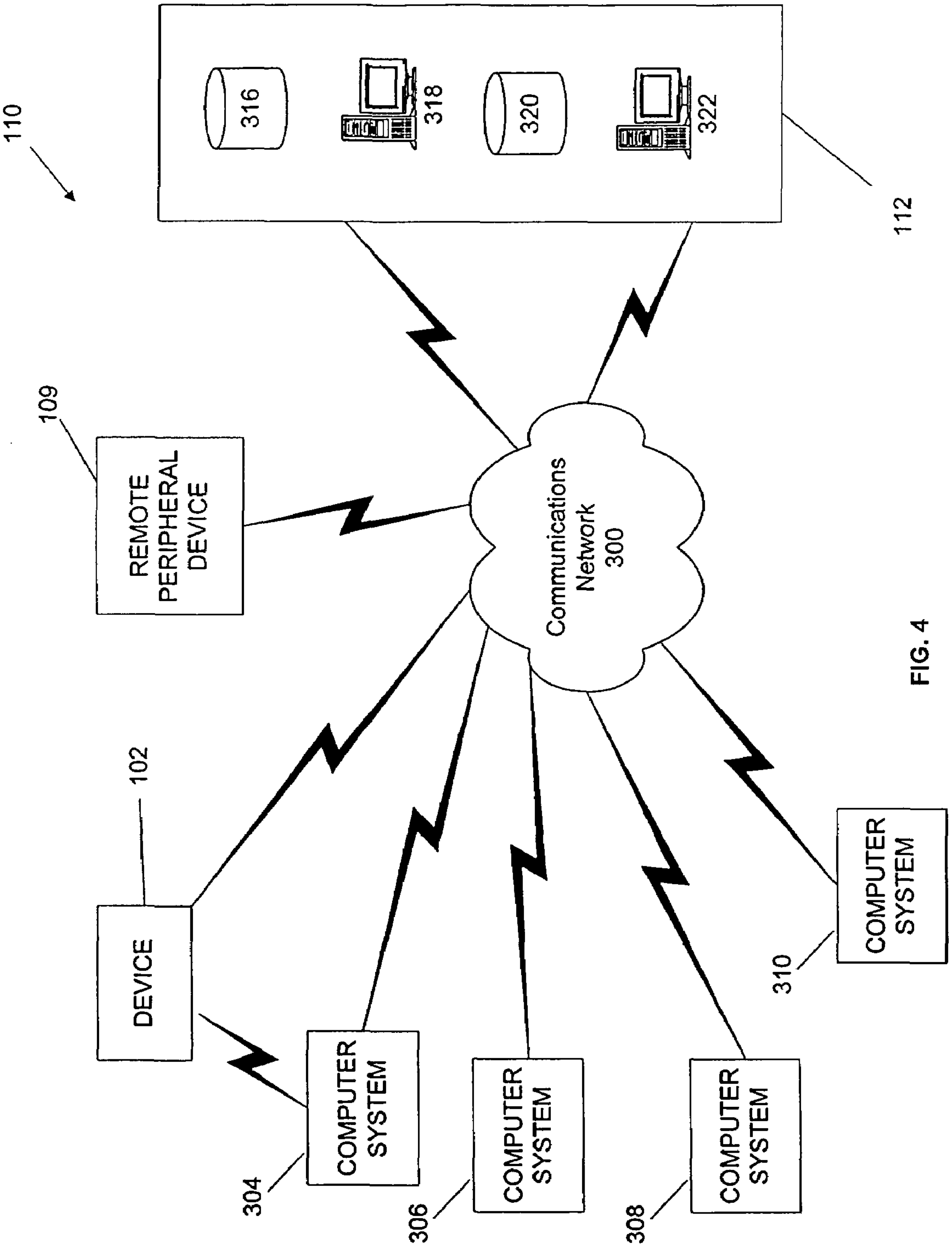
FIG. 4 illustrates an example communication system for use with the advanced patient management system.

Communication system 110 provides for communications between and among the various components of the advanced patient management system 100, such as the devices 102, 104, and 106, host 112, and remote peripheral device 109. FIG. 4 illustrates one embodiment for the communication system 110. The communication system 110 includes a plurality of computer systems 304, 306, 308, and 310, as well as device 102, host 112, and remote peripheral device 109, connected to one another by the communications network 300. The communications network 300 may be, for example, a local area network (LAN), wide area network (WAN), or the Internet. Communications among the various components, as described more fully below, may be implemented using wired or wireless technologies.

In the example embodiment illustrated, the host 112 includes server computers 318 and 322 that communicate with computers 304, 306, 308, and 310 using a variety of communications protocols, described more fully below. The server computers 318 and 322 store information in databases 316 and 320. This information may also be stored in a distributed manner across one or more additional servers.

A variety of communication methods and protocols may be used to facilitate communication between devices 102, 104, and 106, ITU 108, communication system 110, host 112, and remote peripheral device 109. For example, wired and wireless communications methods may be used. Wired communication methods may include, for example and without limitation, traditional copper-line communications such as DSL, broadband technologies such as ISDN and cable modems, and fiber optics, while wireless communications may include cellular, satellite, radio frequency (RF), Infrared, etc.

For any given communication method, a multitude of standard and/or proprietary communication protocols may be used. For example and without limitation, protocols such as radio frequency pulse coding, spread spectrum, direct sequence, time-hopping, frequency hopping, SMTP, FTP, and TCP/IP may be used. Other proprietary methods and protocols may also be used. Further, a combination of two or more of the communication methods and protocols may also be used.

The various communications between the components of the advanced patient management system 100 may be made secure using several different techniques. For example, encryption and/or tunneling techniques may be used to protect data transmissions. Alternatively, a priority data exchange format and interface that are kept confidential may also be used. Authentication can be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 100. Encryption, authentication and verification techniques may also be used to detect and correct data transmission errors.

Communications among the various components of the advanced patient management system 100 may be enhanced using compression techniques to allow large amounts of data to be transmitted efficiently. For example, the devices 102, 104, and 106 or the ITU 108 may compress the recorded information prior to transmitting the information to the ITU 108 or directly to the communication system 110.

The communication methods and protocols described above can facilitate periodic and/or real-time delivery of data.

IV. Host

The example host 112 includes a database module 114, an analysis module 116, and a delivery module 118 (see FIG. 1). Host 112 preferably includes enough processing power to analyze and process large amounts of data collected from each patient, as well as to process statistics and perform analysis for large populations. For example, the host 112 may include a mainframe computer or multi-processor workstation. The host 112 may also include one or more personal computer systems containing sufficient computing power and memory. The host 112 may include storage medium (e.g., hard disks, optical data storage devices, etc.) sufficient to store the massive amount of high-resolution data that is collected from the patients and analyzed.

The host 112 may also include identification and contact information (e.g., IP addresses, telephone numbers, or a product serial number) for the various devices communicating with it, such as ITU 108 and peripheral device 109. For example, each ITU 108 is assigned a hard-coded or static identifier (e.g., IP address, telephone number, etc.), which allows the host 112 to identify which patients information the host 112 is receiving at a given instant. Alternatively, each device 102, 104, and 106 may be assigned a unique identification number, or a unique patient identification number may be transmitted with each transmission of patient data.

When a device is first activated, several methods may be used to associate data received by the advanced patient management system 100 with a given patient. For example, each device may include a unique identification number and a registration form that is filled out by the patient, caregiver, or field representative. The registration form can be used to collect the necessary information to associate collected data with the patient. Alternatively, the user can logon to a web site to allow for the registration information to be collected. In another embodiment, a barcode is included on each device that is scanned prior to or in conjunction deployment of the device to provide the information necessary to associate the recorded data with the given patient.

Referring again to FIG. 1, the example database module 114 includes a patient database 400, a population database 402, a medical database 404, and a general database 406, all of which are described further below.

The patient database 400 includes patient specific data, including data acquired by the devices 102, 104, and 106. The patient database 400 also includes a patient's medical records. The patient database 400 can include historical information regarding the devices 102, 104, and 106. For example, if device 102 is an implantable cardioverter defibrillator (ICD), the patient database 400 records the following device information: P and R measurements, pacing frequency, pacing thresholds, shocking events, recharge time, lead impedance, battery voltage/remaining life, ATR episode and EGMs, histogram information, and other device-specific information. The information stored in the database 400 can be recorded at various times depending on the patient requirements or device requirements. For example, the database 400 is updated at periodic intervals that coincide with the patient downloading data from the device. Alternatively, data in the database 400 can be updated in real time. Typically, the sampling frequency depends on the health condition being monitored and the co-morbidities.

The population database 402 includes non-patient specific data, such as data relating to other patients and population trends. The population database 402 also records epidemic-class device statistics and patient statistics. The population database 402 also includes data relating to staffing by health care providers, environmental data, pharmaceuticals, etc.

The example medical database 404 includes clinical data relating to the treatment of diseases. For example, the medical database 404 includes historical trend data for multiple patients in the form of a record of progression of their disease(s) along with markers of key events.

The general database 406 includes non-medical data of interest to the patient. This can include information relating to news, finances, shopping, technology, entertainment, and/or sports. The general database 406 can be customized to provide general information of specific interest to the patient. For example, stock information can be presented along with the latest health information as detected from the devices 102, 104, and 106.

In another embodiment, information is also provided from an external source, such as external database 600. For example, the external database 600 includes external medical records maintained by a third party, such as drug prescription records maintained by a pharmacy, providing information regarding the type of drugs that have been prescribed for a patient.

The example analysis module 116 includes a patient analysis module 500, device analysis module 502, population analysis module 504, and learning module 506.

Patient analysis module 500 may utilize information collected by the advanced patient management system 100, as well as information for other relevant sources, to analyze data related to a patient and provide timely and predictive assessments of the patient's well-being. In performing this analysis, the patient device module 500 may utilize data collected from a variety of sources, include patient specific physiological and subjective data collected by the advanced patient management system 100, medical and historical records (e.g., lab test results, histories of illnesses, etc., drugs currently and previously administered, etc.), as well as information related to population trends provided from sources external to the advanced patient management system 100.

For example, in one embodiment, the patient analysis module 500 makes a predictive diagnosis of an oncoming event based on information stored in the database module 114. For example, the data continuously gathered from a device of a given patient at a heightened risk for a chronic disease event (such as de-compensations in heart failure) is analyzed. Based on this analysis, therapy, typically device-based or pharmaceutical, is then be applied to the patient either through the device or through clinician intervention.

In another example embodiment, the patient analysis module 500 provides a diagnosis of patient health status and predicted trend based on present and recent historical data collected from a device as interpreted by a system of expert knowledge derived from working practices within clinics.

For example, the patient analysis module 500 performs probabilistic calculations using currently-collected information combined with regularly-collected historical information to predict patient health degradation.

In another example embodiment, the patient analysis module 500 may conduct pre-evaluation of the incoming data stream combined with patient historical information and information from patients with similar disease states. The pre-evaluation system is based on data derived from working clinical practices and the records of outcomes. The derived data is processed in a neural network, fuzzy logic system, or equivalent system to reflect the clinical practice. Further, the patient analysis module 500 may also provide means for periodic processing of present and historical data to yield a multidimensional health state indication along with disease trend prediction, next phase of disease progression co-morbidities, and inferences about what other possible diseases may be involved. The patient analysis module 500 may also integrate data collected from internal and external devices with subjective data to optimize management of overall patient health.

Device analysis module 502 analyzes data from the devices 102, 104, and 106 and ITU 108 to predict and determine device issues or failures. For example, if a medical device 102 fails to communicate at an expected time, device analysis module 502 determines the source of the failure and takes action to restore the performance of the device 102. The device analysis module 502 may also perform additional deterministic and probabilistic calculations. For example, the device analysis module 502 gathers data related to charge levels within a given device, such as an ICD, and provides analysis and alerting functions based on this information if, for example, the charge level reaches a point at which replacement of the device and/or battery is necessary. Similarly, early degradation or imminent failure of medical devices can be identified and proactively addressed, or at-risk devices can be closely monitored.

Population analysis module 504 uses the data collected in the database module 114 to manage the health of a population. For example, a clinic managing cardiac patients can access the advanced patient management system 100 and thereby obtain device-supplied advance information to predict and optimize resource allocation both as to immediate care and as a predictive metric for future need of practicing specialists. As another example, the spread of disease in remote populations can be localized and quarantined rapidly before further spread.

In one embodiment, population analysis module 504 trends the patient population therapy and management as recorded by the devices and directs health care resources to best satisfy the needs of the population. The resources can include people, facilities, supplies, and/or pharmaceuticals. In other embodiments, the population analysis module detects epidemics and other events that affect large population groups. The population analysis module 504 can issue alerts that can initiate a population quarantine, redirect resources to balance size of staffing with number of presenting population, and predict future need of qualified specialists.

The population analysis module 504 may utilize a variety of characteristics to identify like-situated patients, such as, for example, sex, age, genetic makeup, etc. The population analysis module 504 may develop large amounts of data related to a given population based on the information collected by the advanced patient management system 100. In addition, the population analysis module 504 may integrate information from a variety of other sources. For example, the population analysis module 504 may utilize data from public domain databases (e.g., the National Institute of Health), public and governmental and health agency databases, private insurance companies, medical societies (e.g., the American Heart Association), and genomic records (e.g., DNA sequences).

In one embodiment, the host 112 may be used as a "data clearinghouse," to gather and integrate data collected from the devices 102, 104, and 106, as well as data from sources outside the advanced patient management system 100. The integrated data can be shared with other interested entities, subject to privacy restrictions, thereby increasing the quality and integration of data available.

Learning module 506 analyzes the data provided from the various information sources, including the data collected by the advanced patient management system 100 and external information sources. For example, the learning module 506 analyzes historical symptoms, diagnoses, and outcomes along with time development of the diseases and co-morbidities. The learning module 506 can be implemented via a neural network (or equivalent) system.

The learning module 506 can be partially trained (i.e., the learning module 506 may be implemented with a given set of preset values and then learn as the advanced patient management system functions) or untrained (i.e., the learning module 506 is initiated with no preset values and must learn from scratch as the advanced patient management system functions). In other alternative embodiments, the learning module 506 may continue to learn and adjust as the advanced patient management system functions (i.e., in real time), or the learning module 506 may remain at a given level of learning and only advanced to a higher level of understanding when manually allowed to do so.

In a neural network embodiment, new clinical information is presented to create new neural network coefficients that are distributed as a neural network knowledge upgrade. The learning module 506 can include a module for verifying the neural network conclusions for clinical accuracy and significance. The learning module can analyze a database of test cases, appropriate outcomes and relative occurrence of misidentification of the proper outcomes. In some embodiments, the learning module 506 can update the analysis module 116 when the analysis algorithms exceed a threshold level of acceptable misidentifications.

The example learning module 506 uses various algorithms and mathematical modeling such as, for example, trend and statistical analysis, data mining, pattern recognition, cluster analysis, neural networks and fuzzy logic. Learning module 506 may perform deterministic and probabilistic calculations. Deterministic calculations include algorithms for which a clear correlation is known between the data analyzed and a given outcome. For example, there may be a clear correlation between the energy left in a battery of a medical device and the amount of time left before the battery must be replaced.

A probabilistic calculation involves the correlation between data and a given outcome that is less than 100 percent certain. Probabilistic determinations require an analysis of several possible outcomes and an assignment of probabilities for those outcomes (e.g., an increase in weight of a patient may, at a 25% probability, signal an impending de-compensation event and/or indicate that other tests are needed). The learning module 506 performs probabilistic calculations and selects a given response based on less than a 100% probability. Further, as the learning module 506 "learns" for previous determinations (e.g., through a neural network configuration), the learning module 506 becomes more proficient at assigning probabilities for a given data pattern, thereby being able to more confidently select a given response. As the amount of data that has been analyzed by the learning module 506 grows, the learning module 506 becomes more and more accurate at assigning probabilities based on data patterns. A bifurcated analysis may be performed for diseases exhibiting similar symptoms. As progressive quantities of data are collected and the understanding of a given disease state advances, disease analysis is refined where a former singular classification may split into two or more sub-classes.

In addition, patient-specific clinical information can be stored and tracked for hundreds of thousands of individual patients, enabling a first-level electronic clinical analysis of the patient's clinical status and an intelligent estimate of the patient's short-term clinical prognosis. The learning module 506 is capable of tracking and forecasting a patient's clinical status with increasing levels of sophistication by measuring a number of interacting co-morbidities, all of which may serve individually or collectively to degrade the patient's health. This enables learning module 506, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as MI and stroke.

Delivery module 118 coordinates the delivery of feedback based on the analysis performed by the host 112. In response to the analysis module 116, delivery module 118 can manage the devices 102, 104, and 106, perform diagnostic data recovery, program the devices, and otherwise deliver information as needed. In some embodiments, the delivery module 118 can manage a web interface that can be accessed by patients or caregivers. The information gathered by a medical device can be periodically transmitted to a web site that is securely accessible to the caregiver and/or patient in a timely manner. In other embodiments, a patient accesses detailed health information with diagnostic recommendations based upon analysis algorithms derived from leading health care institutions.

For example, the caregiver and/or patient can access the data and analysis performed on the data by accessing one or more general content providers. In one example, the patient's health information is accessed through a general portal such as My Yahoo provided by Yahoo! Inc. of Sunnyvale, Calif. A patient can access his or her My Yahoo homepage and receive information regarding current health and trends derived from the information gathered from the devices 102, 104, and 106, as well as other health information gathered from other sources. The patient may also access other information in addition to health information on the My Yahoo website, such as weather and stock market information. Other electronic delivery methods such as email, facsimile, etc. can also be used for alert distribution.

In an alternative embodiment, the data collected and integrated by the advanced patient system 100, as well as any analysis performed by the system 100, is delivered by delivery module 118 to a caregiver's hospital computer system for access by the caregiver. A standard or custom interface facilitates communication between the advanced patient management system 100 and a legacy hospital system used by the caregiver so that the caregiver can access all relevant information using a system familiar to the caregiver.

The advanced patient management system 100 can also be configured so that various components of the system (e.g., ITU 108, communication system 110, and/or host 112) provide reporting to various individuals (e.g., patient and/or caregiver). For example, different levels of reporting can be provided by (1) the ITU 108 and (2) the host 112. The ITU 108 may be configured to conduct rudimentary analysis of data gathered from devices 102, 104, and 106, and provide reporting should an acute situation be identified. For example, if the ITU 108 detects that a significant heart arrhythmia is imminent or currently taking place, the ITU 108 provides reporting to the patient in the form of an audible or visual alarm.

The host 112 can provide a more sophisticated reporting system. For example, the host 112 can provide exception-based reporting and alerts that categorize different reporting events based on importance. Some reporting events do not require caregiver intervention and therefore can be reported automatically. In other escalating situations, caregiver and/or emergency response personnel need to become involved. For example, based on the data collected by the advanced patient management system 100, the delivery module 118 can communicate directly with the devices 102, 104, and 106, contact a pharmacy to order a specific medication for the patient, and/or contact 911 emergency response. In an alternative embodiment, the delivery module 118 and/or the patient may also establish a voice communication link between the patient and a caregiver, if warranted.

In addition to forms of reporting including visual and/or audible information, the advanced patient management system 100 can also communicate with and reconfigure one or more of the devices 102, 104, and 106. For example, if device 102 is part of a cardiac rhythm management system, the host 112 can communicate with the device 102 and reconfigure the therapy provided by the cardiac rhythm management system based on the data collected from one or more of the devices 102, 104, and 106. In another embodiment, the delivery module 118 can provide to the ITU 108 recorded data, an ideal range for the data, a conclusion based on the recorded data, and a recommended course of action. This information can be displayed on the ITU 108 for the patient to review or made available on the peripheral device 109 for the patient and/or clinician to review.

One or more headings have been provided above to assist in describing the various embodiments disclosed herein. The use of headings, and the resulting division of the description by the headings, should not be construed as limiting in any way. The subject matter described under one heading can be combined with subject matter described under one or more of the other headings without limitation and as desired.

V. Preventing Data Transfer

In some embodiments, the present invention is used in association with a medical device, such as those used with the disease management system described in reference to FIGS. 1-4. Typically, the medical device has some communications capability. For example, the medical device may have long-range communications capability, such as cellular communications capability to communicate with a cellular network or other wireless communications network. The medical device may also have a shorter range communications capability. For example, the medical device may communicate with a local repeater with the local repeater connected through a communications link, such as a telephone line, to the remainder of the disease management system. Some medical devices may also have global positioning system (GPS) capabilities so that the location of the patient may be tracked in addition to recording other physiological patient data.

Although the capabilities and uses of an medical device is without question, there are some drawbacks to the medical device. Some patients may feel as if they are constantly being watched and monitored. For example, a patient with an medical device with GPS capabilities may feel as if his movements are constantly being monitored. Thus, some patients feel a lack of privacy with their medical devices. Many patients desire some private time when their movements and non-essential medical monitoring are not tracked by recording and/or sending the data to a backend system for storage and review. In addition to the location tracking problems involving GPS, medical devices that can provide recording and communication of clinical events can be perceived as also invading the privacy of a patient during selected portions of daily activities. In different embodiments, the present invention provides possible solutions to increase patient comfort while being monitored.

Figure 5:
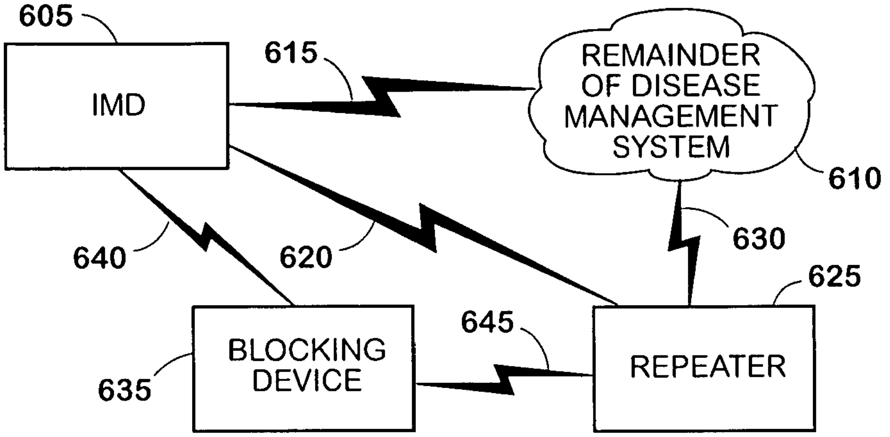
FIG. 5 illustrates an example of the communication system that includes an embodiment of a blocking device that interrupts the transfer of data from the medical device.

Referring now to FIG. 5, examples of a data transfer prevention system for use in the disease management system will be described. An medical device 605 is located either within the body of a patient or on the body of a patient. The medical device 605 may communicate with the remainder of a disease management system 610 via a long-range communications link such as cellular link 615. In another embodiment, the medical device 605 may also communicate via a short-range communications link 620, such as an RF communications link or an inductive coupling, with a local repeater 625. The local repeater may then store and/or send data received from the medical device to the disease management system 610 via a communications link 630. The communications link 630 may be a telephone line, cellular communications link, wireless communications link, etc. A blocking device 635 may also be part of the disease management system to provide the patient with privacy.

As will be described in detail below, in different embodiments the blocking device 635 uses different techniques to provide the patient with privacy. In one embodiment, the blocking device employs jamming technology to produce a jamming signal, such as signal 640, to block the reception of communications by the medical device 605 that are intended to cause the medical device 605 to begin transmitting data. In another embodiment, the blocking device 635 provides an instruction in signal 640 that is received through the communications system of the medical device 605 or provides an instruction signal 645 that is received through a communications system of the repeater device 625 to shutdown the communication of data between the medical device 605 and repeater device 625 when the blocking device is activated. A third embodiment limits the data recorded in the medical device 605 or the repeater device 625 while the blocking device is activated.

In addition to the blocking device 635, other techniques may be utilized to allow the patient to selectively prevent data transfer. For example, the medical device 605 may include a sensor that allows the patient to provide a signal to prevent the medical device 605 from recording and/or transmitting data or an instruction may be provided to the medical device 605 from the repeater 625 to stop recording and/or transmitting data upon the repeater 625 receiving a user input. Alternatively, the external repeater 625 may receive a user input to cause the repeater to stop initiating data transfer with the medical device and/or to stop recording data transmitted by the medical device.

Figure 6:
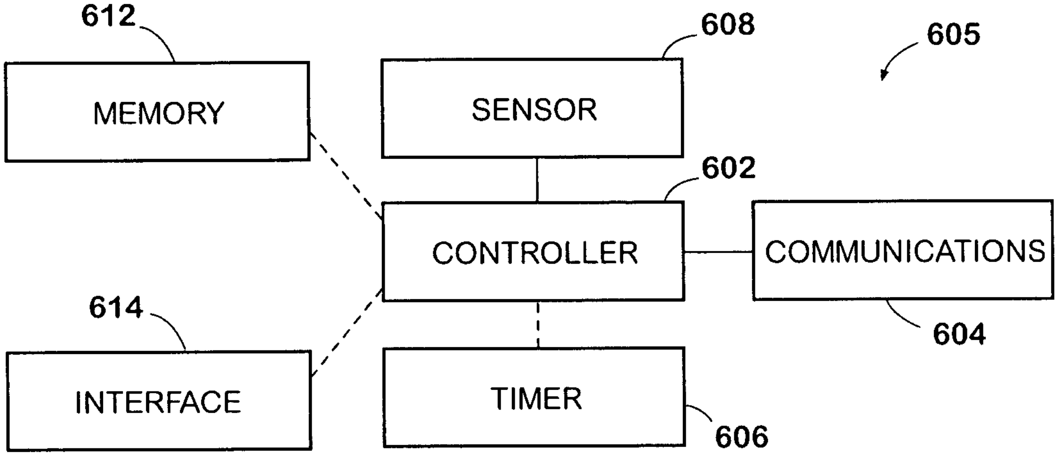
FIG. 6 illustrates an example of the component options of a medical device that allows the patient to control the data transfer.

FIG. 6 shows an medical device 605 that has various components involved in the prevention of data transfer. Various embodiments of the medical device 605 may include all of these components or only a portion of them, depending upon the data prevention scheme being employed. The medical device 605 includes a controller 602 which is one or more logic devices typically present in an medical device. The controller 602 performs logical operations to bring about functions of the medical device 605, such as employing various therapy or monitoring algorithms. Furthermore, the controller 602 may employ data transfer prevention logic to allow the patient to obtain privacy.

The controller 602 interfaces with the various components. The controller interfaces with a communications system 604 that includes the components necessary to communicate with an external device such as a repeater, programmer, and/or a cellular telephone network. The communications system 604 may include a short range RF transceiver, a long range RF transceiver, and/or an inductively coupled transceiver. The controller interfaces with a sensor suite 608, such as an accelerometer, thermocouple, cardiac electrode, or GPS receiver to produce patient data, such as physiological data and/or location data.

The controller 602 may also be linked to one or more components that may or may not be present. Memory space 612 may be present to store patient data that will be transmitted at a later time. Other memory space (not shown) may also be utilized to store programming for the controller 602. The controller 602 may also be interfaced to an input 614 such as a user interface that is used to sense input provided by a patient, such as input to prevent data transfer or to turn data transfer back on, for medical devices that are located externally on the patient's body. Such a user interface may be a touch screen, button, voice recognition, or other similar forms of receiving user input. Additionally, the controller 602 may be interfaced to a timer 606 that allows the controller 602 to keep track of time with respect to various events including those involved in a data transfer prevention scheme. Although not shown, an embodiment of a medical device that is located externally of the patient may also include an alert mechanism, such as a visual or audible indicator, to signal to the patient that a data transfer prevention scheme is active.

Figure 7:
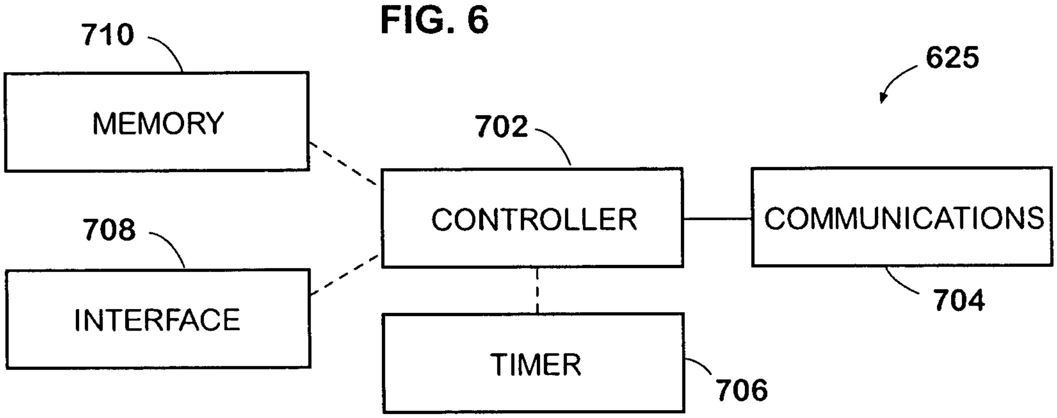
FIG. 7 illustrates an example of the component options of an external repeater device that allows the patient to control the data transfer.

FIG. 7 shows an external repeater device 625 that has various components involved in the prevention of data transfer. Various embodiments of the local external device 625 may include all of these components or only a portion of them, depending upon the data prevention scheme being employed. The external device 625 includes a controller 702 which is one or more logic devices typically present in a repeater device. The controller 702 performs logical operations to bring about functions of the external device 625, such as employing various data soliciting, data forwarding, and medical device programming algorithms. Furthermore, the controller 702 may employ data transfer prevention logic to allow the patient to obtain privacy.

The controller 702 interfaces with the various components. The controller interfaces with a communications system 704 that includes the components necessary to communicate with a medical device, wireline telephone network, a cellular telephone network, and/or a data network. Thus, the communications system is used to communicate with the medical device 605, but in some embodiments the communications system 704 may also be used to communicate over a long range to the disease management system. The communications system 704 may include a short range RF transceiver, a long range RF transceiver, and/or an inductively coupled transceiver.

The controller 702 may also be linked to one or more components that may or may not be present. Memory space 710 may be present to store patient data that will be transmitted at a later time to a remote external device such as a communications system of the remote disease management system. Other memory space (not shown) may also be utilized to store programming for the controller 702. The controller 702 may also be interfaced to a user interface input 708 such as described above for the medical device of FIG. 6 where the user interface 708 is used to sense input provided by a patient, such as input to prevent data transfer by providing a direct instruction to the repeater to stop soliciting, forwarding, and/or storing data. The input may also be used to cause the controller 702 to generate an instruction through the communications system 704 to the medical device to instruct the medical device to stop recording and/or transmitting data. The input 708 may also be used to receive input that turns the data transfer back on. Additionally, the controller 702 may be interfaced to a timer 706 that allows the controller 702 to keep track of time with respect to various events including those involved in a data transfer prevention scheme. Although not shown, an embodiment of an external device may also include an alert mechanism, such as a visual or audible indicator, to signal to the patient that a data transfer prevention scheme is active.

Figure 10:
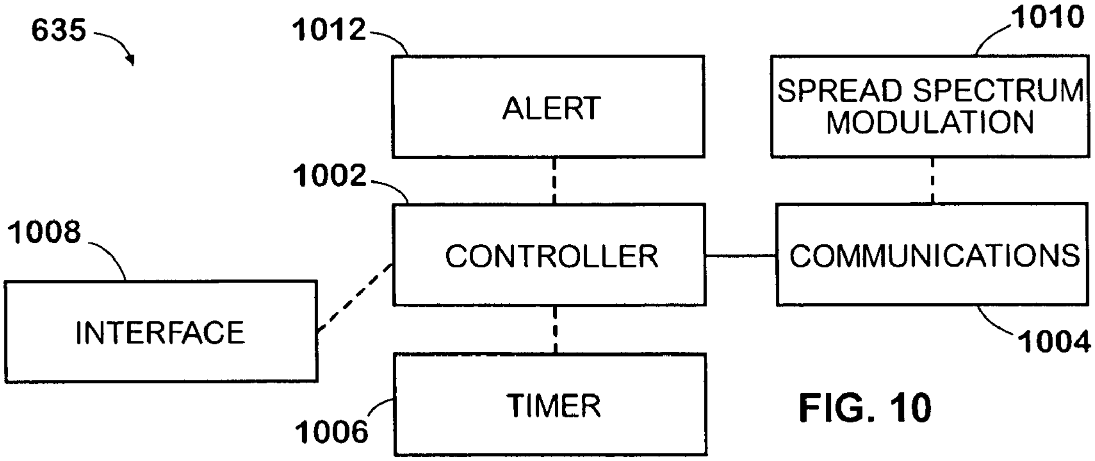
FIG. 10 illustrates an example of the component options of a blocking device such as shown in FIG. 6 to provide jamming of the reception of signals to prevent data transfer from the medical device.

FIG. 10 shows a blocking device 635 that has various components involved in the prevention of data transfer. Various embodiments of the blocking device 635 may include all of these components or only a portion of them, depending upon the data prevention scheme being employed. The blocking device 635 includes a controller 1002 which is one or more logic devices that performs logical operations to bring about functions of the blocking device 635, such as employing various signal jamming or instruction signal algorithms to allow the patient to obtain privacy.

The controller 1002 interfaces with the various components. The controller interfaces with a communications system 1004 that includes the components necessary to communicate with a medical device and/or an external repeater device. The communications system 1004 includes a short range RF transceiver and/or an inductively coupled transceiver. The communications system 1004 may provide a jamming signal to prevent a medical device from receiving a solicitation signal from an external repeater device. Alternatively, the communications system 1004 may provide an instructional signal to the medical device to stop transmitting and/or stop recording or may provide an instructional signal to the external repeater device to stop soliciting, stop forwarding, and/or stop recording. This instructional signal may be a conventional short range RF transmission that encodes data providing the instruction. Alternatively, the instructional signal may be a signal whose presence alone provides the instruction, such as where the communications system 1004 provides a magnetic spike or high frequency RF spike upon the patient placing the blocking device 635 just above the medical device, where the spike is received through an electrode sensor or the communication system of the medical device. The instructional signal may include an identifier of the particular medical device or external device that the signal is intended for so that multiple medical devices may be in range of the blocking device but only an intended medical device stops recording or transmitting data.

To provide jamming, the blocking device 635 transmits a signal from the communications system 1004 that is in proximity to the medical device so that the signal is stronger than a signal being sent by the external device attempting to solicit the medical device for data. For example, the jamming signal may be a signal with a frequency the same as the carrier frequency of an amplitude modulated solicitation from the external device but with a much greater amplitude. The medical device receives the signals, but the solicitation signal appears only as noise due to its significantly lower amplitude than the jamming signal. The jamming signal may be utilized with solicitation signals of other types as well, including FM and spread spectrum. The communications system 1004 may utilize a modulator 1010 to provide the spread spectrum modulation scheme necessary to jam any spread spectrum solicitations from the external device to the medical device.

The controller 1002 may also be linked to one or more components that may or may not be present. The controller 702 may be interfaced to a user interface input 1008 as described above for the medical device of FIG. 6 and external device of FIG. 7 where the user interface 1008 is used to sense input provided by a patient to prevent data transfer by turning the blocking device on to send out the instructional signal to the medical device and/or to the external device or to begin transmitting a jamming signal. The input 1008 may also be used to receive input from the patient to turn the data transfer back on. Additionally, the controller 1002 may be interfaced to a timer 1006 that allows the controller 1002 to keep track of time with respect to various events including those involved in a data transfer prevention scheme so that the blocking signal or instruction signal to stop recording or transmitting data can be automatically stopped after a particular duration. An alert mechanism 1012, such as a visual or audible indicator, may be included to signal to the patient that a data transfer prevention scheme is active. The blocking device, upon sending an instructional signal, may require that the medical device of external device return an acknowledgement signal prior to turning such an indicator on or off to provide verification that the devices are in the intended data prevention mode.

Figure 8:
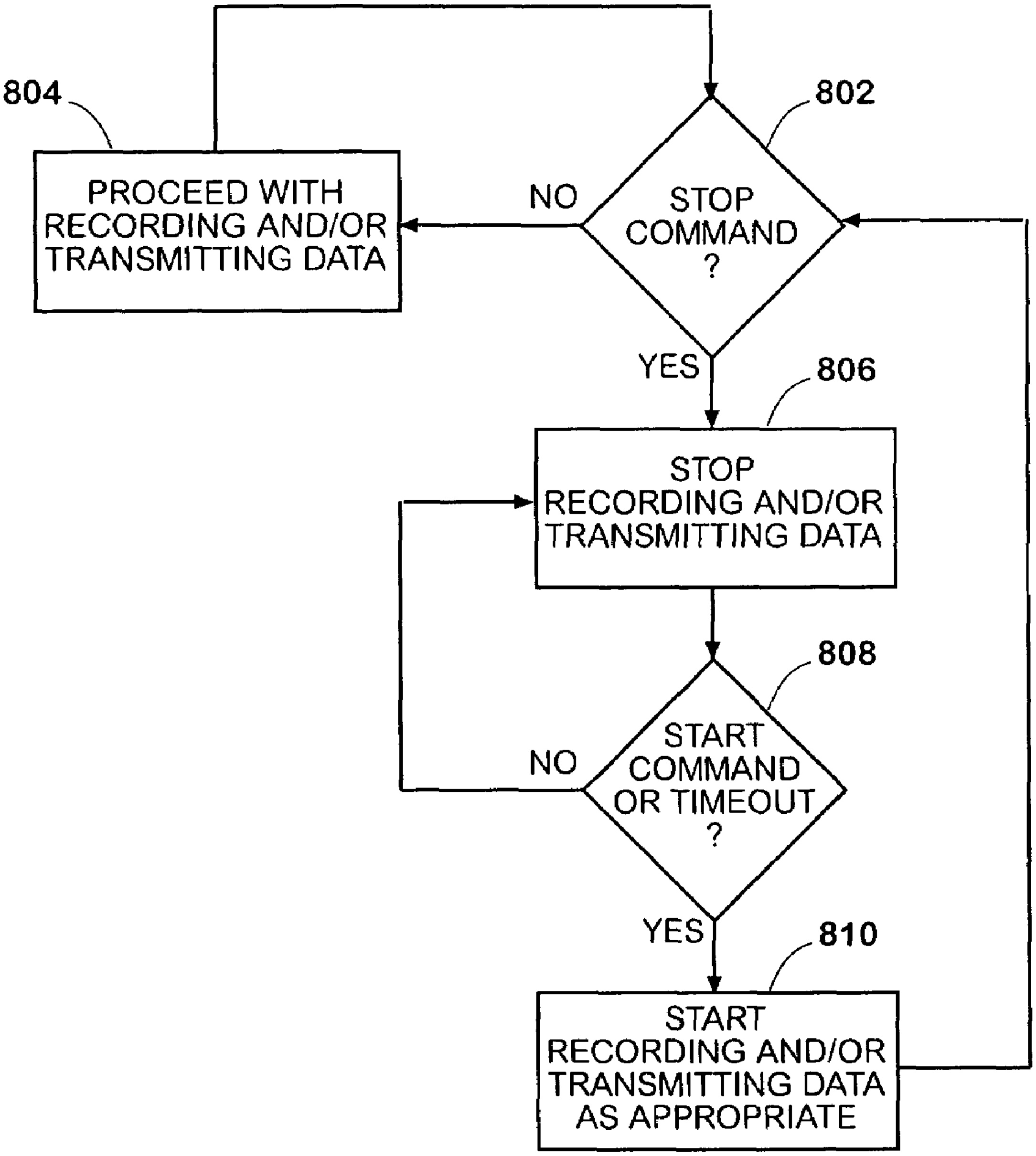
FIG. 8 illustrates the logical operations performed by the medical device to prevent data transfer to external devices or systems.

FIG. 8 shows the logical operations performed by the controller 602 of the medical device 605 to prevent data transfer when the patient has indicated in some way that privacy is desired. The operations begin at query operation 802 where the controller 602 is detecting whether a stop command has been received to prevent data transfer. As has been discussed, this stop command may be received in various ways depending upon the particular embodiment of the medical device being used. For example, this stop command may be received by the patient directly interacting with the medical device by manipulating a user interface of the medical device, or by interacting with the sensor suite of the medical device such as by tapping on the body a pre-determined number of times which is picked up by an accelerometer of the sensor suite. Alternatively, this stop command may be received through a signal from the external repeater device or from the blocking device discussed above, which is likely generated by the patient interacting with the external repeater or the blocking device.

When query operation 802 detects that no stop command has been received, the medical device 605 proceeds as normal at data operation 804 by recording and/or transmitting data as appropriate. However, upon query operation 802 detecting that the stop command has been received, then controller 602 stops the recording and/or transmitting of data at data operation 806. The medical device 605 may be configured to distinguish between a command to stop recording versus a command to stop transmitting data or it may be configured to stop doing one or the other or both for a particular command received. Furthermore, the medical device controller 602 may be configured so that only certain types of data are no longer recorded or transmitted, such as location data and activity data, while life-critical data continues to be recorded and/or transmitted.

After the controller 602 has stopped recording and/or transmitting data, the controller 602 begins to determine whether a start command has been received or a timeout has occurred at query operation 808. For example, a start command may be generated by a patient interacting directly with the medical device again to re-start data transfer through beginning data recording or data transmission at that time. Additionally, a start command may be generated by a signal from the external repeater device or blocking device and may take the form of an actual data command, the presence of a particular signal, or the lack of a particular signal. Such a signal, or lack thereof, may result from a patient interacting with the external repeater or blocking device to cause the start command to occur. Additionally, for embodiments of the external repeater or blocking device that includes a timer and timeout logic, the start command may result from the pre-defined timeout occurring at the external device or blocking device.

A timeout may be detected at query operation 808 for embodiments of a medical device that also utilizes a timer and a controller with logic to detect whether the pre-defined timeout has occurred since the stop command was issued. Once the start command or timeout is detected at query operation 808, then the controller 602 re-starts the recording and/or data transmission as appropriate to restore data transfer for the medical device. Operational flow then returns to query operation 802 where the controller 602 again begins looking for a stop command.

Figure 9:
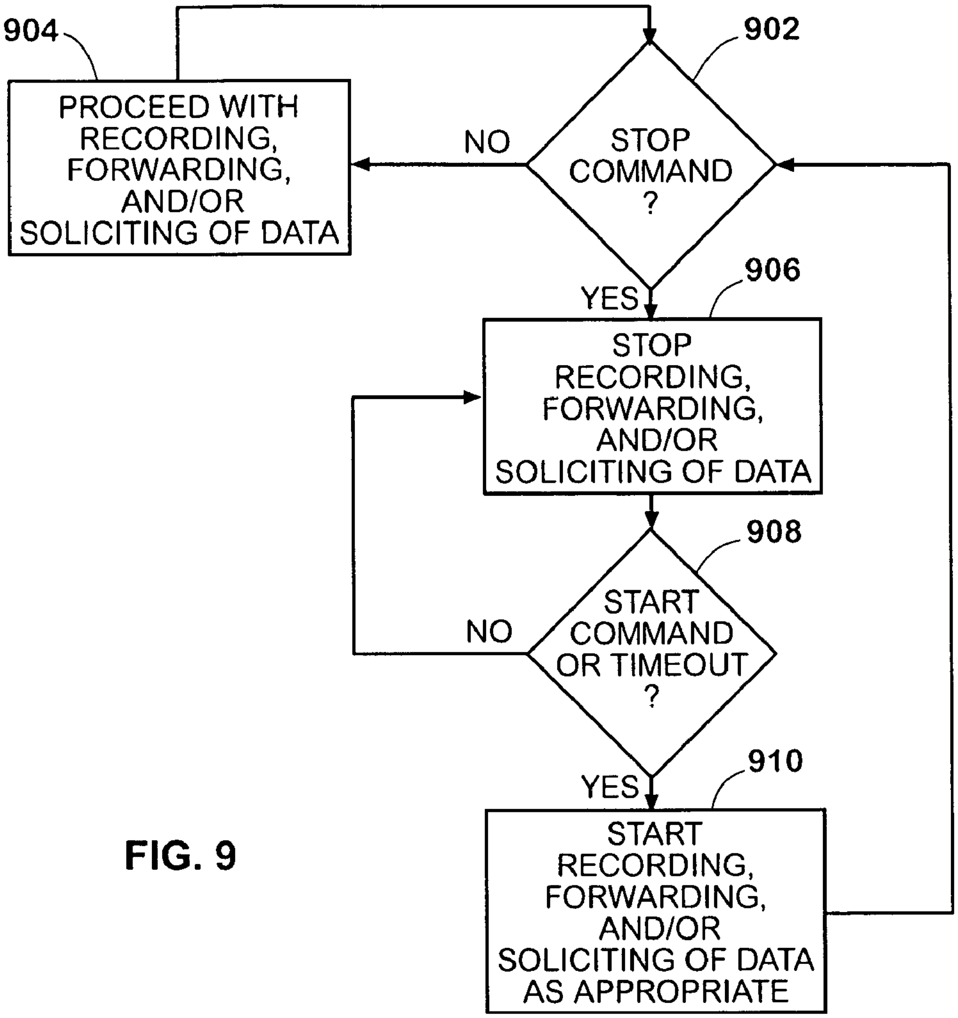
FIG. 9 illustrates the logical operations performed by the external repeater device to prevent data transfer to external devices or systems.

FIG. 9 shows the logical operations performed by the controller 702 of the external repeater 625 to prevent data transfer when the patient has indicated in some way that privacy is desired. The operations begin at query operation 902 where the controller 702 is detecting whether a stop command has been received to prevent data transfer. As has been discussed, this stop command may be received in various ways depending upon the particular embodiment of the external device being used. For example, this stop command may be received by the patient directly interacting with the external device by manipulating a user interface of the external device. Alternatively, this stop command may be received through a signal from the blocking device discussed above, which is likely generated by the patient interacting with the blocking device.

When query operation 902 detects that no stop command has been received, the external device 625 proceeds as normal at data operation 904 by soliciting for, recording of, and/or forwarding data as appropriate. However, upon query operation 902 detecting that the stop command has been received, then controller 702 stops the soliciting for, recording of, and/or forwarding of data at data operation 906. The external device 625 may be configured to distinguish between a command to stop recording versus a command to stop transmitting data or it may be configured to stop doing one or the other or both for a particular command received. Furthermore, the device controller 702 may be configured so that only certain types of data are no longer solicited for, recorded, and/or transmitted, such as location data and activity data, while life-critical data continues to be solicited for, recorded, and/or forwarded.

After the controller 702 has stopped soliciting for, recording, and/or forwarding data, the controller 702 begins to determine whether a start command has been received or a timeout has occurred at query operation 908. For example, a start command may be generated by a patient interacting directly with the external device again to re-start data transfer through beginning the solicitation for, recording of, or forwarding of data at that time. Additionally, a start command may be generated by a signal from the blocking device and may take the form of an actual data command, the presence of a particular signal, or the lack of a particular signal. Such a signal, or lack thereof, may result from a patient interacting with the blocking device to cause the start command to occur. Additionally, for embodiments of the blocking device that includes a timer and timeout logic, the start command may result from the pre-defined timeout occurring at the blocking device.

A timeout may be detected at query operation 908 for embodiments of an external repeater that also utilizes a timer and a controller with logic to detect whether the pre-defined timeout has occurred since the stop command was issued. Once the start command or timeout is detected at query operation 908, then the controller 702 re-starts the solicitation for, recording of, and/or forwarding of data as appropriate to restore data transfer. Operational flow then returns to query operation 902 where the controller 702 again begins looking for a stop command.

As can be seen from the discussion above and the associated drawings, the patient may initiate privacy by interacting with the medical device, external device, and/or blocking device depending upon the particular embodiments of those devices that are present. The patient may further interact with those devices to end the privacy period, or for embodiments where pre-defined timeout periods and timers are in use, the devices themselves may automatically end the privacy period upon reaching the timeout. Accordingly, the patient may benefit from the medical device while being able to control privacy.

The logical operations of FIGS. 8 and 9 for the medical device and external repeater, those discussed above for the blocking device, and those related to various other embodiments of the present invention may be implemented (1) as a sequence of processor implemented acts or program modules running on a processing system of the external device 625, medical device 605, and blocking device 635 and/or (2) as interconnected machine logic circuits or circuit modules within the processing systems. The implementation is a matter of choice dependent on the performance requirements of the processing system(s) implementing the invention. Accordingly, the logical operations making up the embodiments of the present invention described herein are referred to variously as operations, acts or modules. It will be recognized by one skilled in the art that these operations, acts, and modules may be implemented in software, in firmware, in special purpose digital logic, and any combination thereof without deviating from the spirit and scope of the present invention as recited within the claims attached hereto.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

What is claimed is:

1. A method for jamming communications between an implantable medical device and an external communications device to prevent data transfer, the method comprising;

receiving an external input at an external blocking device to begin jamming the communications between the implantable medical device and the external communications device;

transmitting a jamming signal from the external blocking device to jam the communications between the implantable medical device and the external communications device, wherein the jamming signal is selected to target a particular frequency range selected for use in the communications between the implantable medical device and the external communications device; and using the jamming signal, jamming communications between the implantable medical device and the external communications device to prevent data transfer between the implantable medical device and the external communications device.

2. The method of claim 1, wherein the external blocking device includes a short range jamming transmitter.

3. The method of claim 1, wherein the jamming signal blankets the frequency range used for the communications.

4. The method of claim 2, wherein the short range jamming transmitter is in proximity to the implantable medical device and wherein transmitting a jamming signal from the external blocking device to jam the communications comprises preventing the implantable medical device from receiving a solicitation to begin transmitting that is sent by the external communications device.

5. The method of claim 1, wherein the communications occur through a cellular phone system employing control channels and the jamming signal blankets the control channels used for the communications.

6. The method of claim 1, wherein the input is received in response to manipulating a user interface at the external blocking device.

7. The method of claim 1, further comprising providing an indication of jamming, wherein the indication is a visual indication on the external blocking device.

8. The method of claim 1, further comprising providing an indication of jamming, wherein the indication is an auditory signal transmitted by the external blocking device.

9. The method of claim 1, further comprising determining whether a specified period of time has passed and, if so, then ceasing to transmit the jamming signal.

10. The method of claim 1, wherein the communications comprise communications related to electively recorded physiological patient data.

11. The method of claim 1, in which the jamming signal is operable to prevent reception of communications by the implantable medical device.

12. The method of claim 11, in which the jamming signal is operable to prevent reception of communications by the implantable medical device that are intended to cause the implantable medical device to begin transmitting data.

13. A method for inhibiting communications between an implantable medical device and an external communications device to prevent data transfer, the method comprising:

receiving at an external location an external input to begin inhibiting the communications between the implantable medical device and the external communications device, wherein the external input is configured to instruct the external communications device to cease sending a solicitation for data to the implantable medical device; and upon receiving the input, ceasing to establish data transmission to the external communications device of the data generated from the implantable medical device.

14. The method of claim 13, wherein the input is received at the external communications device and ceasing data transfer comprises ceasing sending a solicitation for data from the external communications device to the implantable medical device.

15. The method of claim 13, wherein the input is received at an external blocking device and wherein ceasing data transmission comprises sending a communication from the external blocking device to the external communications device instructing the external communications device to cease sending a solicitation for data to the implantable medical device.

16. The method of claim 15, comprising generating an indication of inhibited communications, wherein the indication is a visual indication on the external blocking device.

17. The method of claim 15, comprising generating an indication of inhibited communications, wherein the indication is an auditory signal transmitted by the external blocking device.

18. The method of claim 13, further comprising determining whether a specified period of time has passed and, if so, then no longer ceasing to establish data transmission from the implantable medical device to the external communications device.

19. The method of claim 13, wherein the data transmission comprises communications related to electively recorded physiological patient data.

20. A method for inhibiting communications between an implantable medical device and an external communications device to prevent data transfer, the method comprising:

receiving at an external location an external input to begin inhibiting the communications between the implantable medical device and the external communications device wherein the input is received at the implantable medical device though a physiological sensor and wherein ceasing to establish data transmission comprises stopping transmitting of communications from the implantable medical device; and upon receiving the input, ceasing to establish data transmission to the external communications device of the data generated from the implantable medical device.

21. The method of claim 20, wherein the input comprises a signal at an accelerometer of the implantable medical device.

22. The method of claim 21 wherein the signal received at the accelerometer comprises a series of taps on a patient's body.

23. An implantable medical device, comprising:

an implantable communications system that sends and receives signals;

at least one implantable physiological sensor that detects physiological information about a patient to produce data;

an implantable controller configured to detect an input at the at least one physiological sensor indicating that data transmission should cease, and to cease transmitting data though the communication system upon detecting the input.

24. The medical device of claim 23, wherein the at least one physiological sensor comprises an accelerometer, and wherein the input is a signal from the accelerometer resulting from taps by a patient wearing the medical device.

25. The medical device of claim 23, further comprising a timer, and wherein the controller detects from the timer the amount of time that data transmission has ceased and restarts data transmission upon the expiration of a pre-defined interval.

26. A system for inhibiting communications between an implantable medical device and an external device to prevent data transfer therebetween, the system comprising:

means for receiving an external input to a physiological sensor to begin inhibiting the communications between the implantable medical device and the external device; and means for, upon receiving the input, ceasing to establish data transmission to the external device of the data generated from the implantable medical device.

* * * * *

UNITED STATES PATENT AND TRADEMARK OFFICE

CERTIFICATE OF CORRECTION

PATENT NO. : 7,289,761 B2
APPLICATION NO. : 10/601966
DATED : October 30, 2007
INVENTOR(S) : Mazar It is certified that error appears in the above-identified patent and that said Letters Patent is hereby corrected as shown below:

In column 24, line 36, in Claim 20, delete “though” and insert -- through --, therefor.

In column 24, line 60, in Claim 23, delete “though” and insert -- through --, therefor.

Signed and Sealed this

Fifteenth Day of April, 2008

JON W. DUDAS
*Director of the United States Patent and Trademark Office*